United States Patent [19]

Ohtsuki et al.

[11] Patent Number: 5,108,735

[45] Date of Patent: Apr. 28, 1992

[54] ORAL COMPOSITION

[75] Inventors: Hidehiko Ohtsuki; Sayuri Tanii, both of Takatsuki; Satoko Ozawa, Ikeda, all of Japan

[73] Assignee: Sunstar Kabushiki Kaisha, Osaka, Japan

[21] Appl. No.: 474,110

[22] PCT Filed: Sep. 6, 1989

[86] PCT No.: PCT/JP89/00917

§ 371 Date: May 3, 1990

§ 102(e) Date: May 3, 1990

[87] PCT Pub. No.: WO90/02544

PCT Pub. Date: Mar. 22, 1990

[30] Foreign Application Priority Data

Sep. 9, 1988 [JP] Japan ............... 63-227059
Sep. 9, 1988 [JP] Japan ............... 63-227060

[51] Int. Cl.$^5$ ............... A61K 7/16; A61K 7/28; A61K 7/22
[52] U.S. Cl. ............... 424/50; 424/54
[58] Field of Search ............... 424/49–58

[56] References Cited

U.S. PATENT DOCUMENTS

| | | | |
|---|---|---|---|
| 4,466,954 | 8/1984 | Ichikawa et al. | 424/50 |
| 4,469,673 | 9/1984 | Ioka et al. | 424/50 |
| 4,576,816 | 3/1986 | Suganuma et al. | 424/50 |
| 4,585,648 | 4/1986 | Maeyama et al. | 424/50 |
| 4,645,662 | 2/1987 | Nakashima et al. | 424/50 |
| 4,725,428 | 2/1988 | Miyahara et al. | 424/50 |
| 4,911,918 | 3/1990 | Kiyoshige et al. | 424/50 |

FOREIGN PATENT DOCUMENTS

| | | |
|---|---|---|
| 394470 | 10/1990 | European Pat. Off. . |
| 59-152314A | 8/1984 | Japan . |
| 59-152314 | 8/1984 | Japan . |
| 59-152315 | 8/1984 | Japan . |
| 59-152315A | 8/1984 | Japan . |
| 59-152316A | 8/1984 | Japan . |
| 61-176518 | 8/1986 | Japan . |
| 1-036802B | 8/1989 | Japan . |
| 1-053847B | 11/1989 | Japan . |
| 90/02544 | 3/1990 | PCT Int'l Appl. . |

OTHER PUBLICATIONS

Sunstar CA. 101:235407F (1984) of JPN. 59152314 Aug. 31, 1984.
Sunstar CA. 101:235408G (1984) of JPN 59152315 Aug. 31, 1984.
Sunstar CA. 101:235409H (1984) of JPN 59152316 Aug. 31, 1984.
Sunstar CA. 101:235410B (1984) of JPN 59152317 Aug. 31, 1984.
Otsuki CA. 112:240332J (1990) of JPN 02045415 Feb. 15, 1990.
Otsuki CA. 113:46142C (1990) of JPN 02045412 Feb. 15, 1990.
Otsuki CA. 113:46143D (1990) of JPN 02045414 Feb. 15, 1990.
Otsuki CA. 113:217823G (1990) of PCT/WO 9002544 Mar. 22, 1990.
Patent Abstracts of Japan, vol. 8, No. 283, Dec. 25, 1984, 59-152315.
Patent Abstracts of Japan, vol. 12, No. 209, Jun. 15, 1988, 63-8326.
Patent Abstracts of Japan, vol. 12, No. 47, Feb. 12, 1988, 62-195320.

*Primary Examiner*—Shep K. Rose
*Attorney, Agent, or Firm*—Wegner, Cantor, Mueller & Player

[57] ABSTRACT

An oral composition comprising mutanase and, as surfactants, a N-acyl sarcosinate or a N-acyl-L-glutamate together with one or more of nonionic surfactants selected from the group consisting of polyoxyethylene sorbitol fatty acid ester, polyoxyethylene glycerin fatty acid ester, polyoxyethylene alkyl ether, polyoxyethylene lanolin derivative, polyoxyethylene nonyl phenyl formaldehyde condensate, polyoxyethylene-polyoxypropylene block copolymer, polyoxyethylene sorbitan fatty acid ester, polyoxyethylene hydrogenated castor oil, polyoxyethylene castor oil and polyethylene glycol fatty acid ester.

3 Claims, No Drawings

ORAL COMPOSITION

FIELD OF THE INVENTION

The present invention relates to a composition for the oral cavity. More particularly, it relates to an oral composition such as dentifrice, dental rinse, mouthwash, dental paste or denture cleanser wherein mutanase which is a pharmacologically active agent for preventing dental caries is stably formulated.

PRIOR ART

Heretofore, as one of mechanisms for developing dental caries, it has been pointed out that *Streptococcus mutans* which is etiogenic bacteria of dental caries produces a water-insoluble and adhesive glucan having α-1,3-glucoside bond (mutan) from sucrose and strongly adheres to the surfaces of teeth to produce lactic acid thereon, which results in decalcification of teeth (Clinical Bacteriology, Vol. 1, page 24, 1974). Mutanase is an enzyme which breaks α-1,3-glucoside bond of the glucan produced by *Streptococcus mutans* and a trial to prevent dental caries has been made by utilizing the activity of the enzyme to decompose the glucan to inhibit adhesion of *Streptococcus mutans* to the surfaces of teeth (Journal of Dental Research, Vol. 5, supplement, page 394, 1972). Mutanase used therein is derived from *Trichlderma harzianum*. However, in addition to this, the enzyme derived from bacteria belonging to the genus *Flavobacterium* (Japanese Patent Kokoku No. 52-38113), *Pseudomonas* (Japanese Patent Kokoku No. 56-1070) or the like is also reported. Further, to formulate mutanase in dentifrices is also proposed (Japanese Patent Kokoku No. 55-50006 and Japanese Patent Kokoku No. 57-36890) and it is admitted that mutanase is useful for preventing dental caries. However, mutanase is extremely unstable in the presence of water and a surfactant and is labilized by alterations in pH and, therefore, its enzymatic activity is liable to be lost. On the other hand, for example, a surfactant is generally an essential ingredient as a foaming agent, dispersant and/or detergent in an oral composition and, therefore, it is very difficult to formulate mutanase in such a composition. Under these circumstances, in Japanese Patent Kokai No. 59-152314 and Japanese Patent Kokai No. 59-152315, there is proposed that mutanase is stably formulated in an oral composition by using a N-acyl sarcosinate or a combination of a N-acyl sarcosinate with a sucrose fatty acid ester.

OBJECTS OF THE INVENTION

In order to improve the stability of mutanase formulated in an oral composition, the present inventors have studied intensively by adding a nonionic surfactant as a foaming auxiliary to a N-acyl sarcosinate which shows "juice effect" and has excellent feeling of use to obtain an oral composition having excellent feeling of use, foaming properties and stability. As a result, it has been found that, by using a specific nonionic surfactant, the stabilization of mutanase can be obtained in the same degree as or more improved degree than that obtained by a combination of a N-acyl sarcosinate with a sucrose fatty acid ester.

Further, since a N-acyl sarcosinate may cause detachment of oral mucosa depending on its amount formulated, the amount thereof in a dentifrice is limited to not more than 0.5% by weight and therefore the use thereof is extremely limited. However, mutanase can be stabilized by using a N-acyl-L-glutamate instead of a N-acyl sarcosinate and using it in combination with the specific nonionic surfactant.

The present invention is baste on this knowledge and provides an oral composition wherein mutanase is stably formulated.

SUMMARY OF THE INVENTION

The present invention is characterized in that, in an oral composition containing mutanase, a N-acyl sarcosinate or a N-acyl-L-glutamate is formulated as a surfactant together with one or more of nonionic surfactants selected from the group consisting of polyoxyethylene sorbitol fatty acid ester, polyoxyethylene glycerin fatty acid ester, polyoxyethylene alkyl ether, polyoxyethylene lanolin derivative, polyoxyethylene nonyl phenyl formaldehyde condensation product, polyoxyethylene-polyoxypropylene block copolymer, polyoxyethylene sorbitan fatty acid ester, polyoxyethylene hydrogenated castor oil, polyoxyethylene castor oil and polyethylene glycol fatty acid ester. According to the present invention, mutanase formulated in the oral composition can maintain its sufficient enzymatic activity for a long period of time and excellent effect for preventing dental caries can be elicited.

DETAILED DESCRIPTION OF THE INVENTION

The N-acyl sarcosinate to be used is represented by the formula:

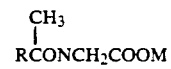

wherein R is an alkyl group and M is an alkali metal or ammonium, and the alkyl group R is preferably that having 11 to 17 carbon atoms in view of solubility and dispersibility of other ingredients. Further, as the group M which forms a salt, sodium, potassium and ammonium are preferable in view of availability thereof. Typical examples of N-acyl sarcosinate include N-lauroyl sarcosinate, N-myristoyl sarcosinate, N-palmitoyl sarcosinate, N-stearoyl sarcosinate and the like. Usually, N-acyl sarcosinate is formulated in an amount of not more than 3000-fold based on the amount of mutanase to be formulated and in an amount of 0.01 to 3% by weight based on the total weight of the composition.

The N-acyl-L-glutamate to be used is represented by the formula:

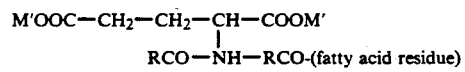

wherein M' is a salt forming group. As the varieties of the fatty acids, there are coconut oil fatty acid, lauric acid, stearic acid (hydrogenated tallow), distilled coconut oil fatty acid, mixed fatty acids (hydrogenated tallow and coconut oil) and the like and, as the salt forming group, monosodium, triethanolamine and disodium are preferable in view of availability. Typical examples of the N-acyl-L-glutamates include monosodium N-lauroyl-L-glutamate, monosodium N-coconut oil fatty acid acyl-L-glutamate, monotriethanolamine N-coconut oil fatty acid acyl-L-glutamate, monosodium N-stearoyl-L-glutamate and the like. Usually, the N-acyl-L-glutamate is formulated in an amount of not more than 3000-fold based on the amount of mutanase to be formulated and in an amount of 0.01 to 3% by weight based on the total weight of the composition.

As the polyoxyethylene (POE) sorbitol fatty acid ester to be used, there are those wherein the addition molar number of ethylene oxide is 5 to 60 and the number of carbon atoms of the fatty acid is 12 to 18, typically, POE (60 mol) sorbitol tetraoleate, POE (60 mol) sorbitol tetrastearate and POE (6 mol) sorbitol monolaurate. As the polyoxyethylene glycerin fatty acid ester to be used, there are those wherein the addition molar number of ethylene oxide is 5 to 20 and the number of carbon atoms of the fatty acid is 8 to 18, typically, POE (15 mol) glyceryl monooleate and POE (15 mol) glyceryl monostearate. As the polyoxyethylene alkyl ether, there are those wherein the addition molar number of ethylene oxide is 2 to 50 and the number of carbon atoms of the alkyl is 12 to 22, typically, POE (9 mol) lauryl ether, POE (15 mol) cetyl ether and POE (10 mol) oleyl ether. As the polyoxyethylene lanolin derivative, there are those wherein the addition molar number of ethylene oxide is 1 to 100, typically, POE (30 mol) lanolin and POE (40 mol) lanolin alcohol. As the polyoxyethylene nonyl phenyl formaldehyde condensate, there are those wherein the addition molar number of ethylene oxide is 1 to 50, typically, POE (20 mol) nonyl phenyl formaldehyde condensate. As the polyoxyethylene (POE)-polyoxypropylene (POP) block copolymer, there are those wherein the average polymerization degree of ethylene oxide is 190 to 260 and the average polymerization degree of propylene oxide is 50 to 70, typically, POE (196 mol) POP (67 mol) block copolymer. As the polyoxyethylene sorbitan fatty acid ester, there are those wherein the addition molar number of ethylene oxide is 5 to 30 and the number of carbon atoms of fatty acid is 12 to 18, typically, POE (20 mol) sorbitan monostearate and POE (20 mol) sorbitan monooleate. As the polyoxyethylene hydrogenated castor oil, there are those wherein the degree of polymerization of ethylene oxide is 5 to 100, typically, POE (50 mol) hydrogenated castor oil, POE (60 mol) hydrogenated castor oil and POE (80 mol) hydrogenated castor oil. As the polyoxyethylene castor oil, there are those wherein the degree of polymerization of ethylene oxide is 3 to 70, typically, POE (60 mol) castor oil and POE (50 mol) castor oil. As the polyethylene glycol fatty acid ester, there are those wherein the molecular weight of polyethylene glycol is 40 to 2800 and the number of carbon atoms of the fatty acid is 12 to 18, typically, POE (40 mol) monostearate and POE (45 mol) monostearate. These nonionic surfactants can be used alone or in combination thereof.

Usually, these nonionic surfactants are formulated in an amount that the weight ratio of the N-acyl sarcosinate to the nonionic surfactant is not more than 5:1 (in the direction of decrease in the amount of the N-acyl sarcosinate) or the weight ratio of the N-acyl-L-glutamate to the nonionic surfactant is not more than 9:1 (in the direction of decrease in the amount of the N-acyl-L-glutamate) in view of stabilization of mutanase, and the amount of the nonionic surfactant is preferably not more than 3% by weight based on the total weight of the composition.

Further, when the stability of the system of the composition is taken into consideration, the total amount of the N-acyl sarcosinate and the nonionic surfactant are preferably not more than 4% by weight and the total amount of the N-acyl-L-glutamate and the nonionic surfactant are preferably not more than 5% by weight.

Any mutanase having $\alpha$-1,3-glucosidase activity can be used regardless of its microbial origin. Examples thereof which can usually be available include those obtained by cultivating mutanase-producing bacteria such as *Trichoderma harzianum* OMZ779, *Cladosporium reginne* QM7998, *Streptomyces velensis*, *Aspergillus nidulans*, *Flavobacterium sp.* or *Pseudomonas sp.* in a culture medium containing normal nutrients or a culture medium wherein $\alpha$-1,3-glucan is further added in addition to normal nutrients, or those obtained by gene-manipulating mutanase-producing bacteria and fractionating the resulting supernatant of the culture solution containing mutanase by salting-out method, adsorption method, solvent fractionation method or the like. In general, although mutanase slightly varies in properties depending upon a particular kind of producer, usually, it is characterized in that the optimum pH thereof is in an acidic side and the activity thereof is to solubilize mutan by decomposition to release reducing sugars.

In the present invention, usually, the desirable effect for preventing dental caries can be obtained by formulating 1,000 to 1,000,000 units/g of mutanase in an amount of 0.001 to 10% by weight based on the total weight of the composition.

By the way, one unit of mutanase is defined as the amount of the enzyme for decomposition of mutan in 0.1 M acetic acid buffer solution (pH 5.7) at 40° C. to release 1 $\mu$M of reducing sugars as glucose per one minute.

The composition for the oral cavity of the present invention can be prepared in the form of dentifrice, dental rinse, mouthwash, paste, denture cleanser and the like according to a conventional method. Other ingredients are not specifically limited and they may be any ingredients which can be used in this kind of compositions. For example, in the case of toothpaste, polishing agents, binders, humectants, sweeteners, flavors, preservatives and other pharmacologically active agents can be appropriately formulated.

Next, the results of experiments for stabilization of mutanase by using the N-acyl sarcosinate in combination with the nonionic surfactant are illustrated.

EXPERIMENT 1

Mutanase (17 mg, 6,500 units/g) derived from *Pseudonomas sp.* strain (FERM P-4273) was dissolved in 0.1 M acetate buffer solution (500 ml, pH 5.7) to obtain an enzyme solution. The enzyme solution (10 ml) was admixed with each solution (10 ml) of various surfactants as shown in Table 1. The mixture was allowed to stand at 25° C. in a water bath for 3 hours and then enzymatic activity in the mixture was determined. By taking the initial mutanase activity in a reaction system containing no surfactant as 100%, a relative ratio of mutanase activity in a reaction system containing the surfactant was determined. The results are shown in Table 1.

TABLE 1

| Anion | Nonion | Amount of enzyme (wt %) | Surfactant Amount of anion (wt %) | Surfactant Amount of nonion (wt %) | Ratio of enzyme/surfactant Anion | Ratio of enzyme/surfactant Nonion | Ratio of anion/nonion | Ratio of activity (%) |
|---|---|---|---|---|---|---|---|---|
| no surfactant is added | | 0.0017 | — | — | — | — | — | 100 |
| Sodium L-lauroyl-sarcosinate | POE(60) sorbitol tetraoleate | 0.0017 | 0.51 | 0.51 | 1/300 | 1/300 | 1:1 | 93 |
| Sodium L-lauroyl-sarcosinate | POE(15) glycerin monostearate | 0.0017 | 0.51 | 0.51 | 1/300 | 1/300 | 1:1 | 99 |
| Sodium L-lauroyl-sarcosinate | POE lanolin | 0.0017 | 0.51 | 0.51 | 1/300 | 1/300 | 1:1 | 91 |
| Sodium L-lauroyl-sarcosinate | POE nonyl phenyl formaldehyde condensate | 0.0017 | 0.51 | 0.51 | 1/300 | 1/300 | 1:1 | 98 |
| Sodium L-lauroyl-sarcosinate | POE(196) POP(67) block copolymer | 0.0017 | 0.51 | 0.51 | 1/300 | 1/300 | 1:1 | 90 |
| Sodium L-lauroyl-sarcosinate | POE(20) sorbitan monooleate | 0.0017 | 0.51 | 0.51 | 1/300 | 1/300 | 1:1 | 91 |
| Sodium L-lauroyl-sarcosinate | POE(20) hydrogenated castor oil | 0.0017 | 0.51 | 0.51 | 1/300 | 1/300 | 1:1 | 89 |
| Sodium L-lauroyl-sarcosine | POE(60) castor oil | 0.0017 | 0.51 | 0.51 | 1/300 | 1/300 | 1:1 | 92 |
| Sodium L-lauroyl-sarcosine | POE(40) monostearate | 0.0017 | 0.51 | 0.51 | 1/300 | 1/300 | 1:1 | 89 |
| Sodium L-lauroyl-sarcosine | POE(9) lauryl ether | 0.0017 | 0.51 | 0.51 | 1/300 | 1/300 | 1:1 | 95 |
| Sodium L-lauroyl-sarcosine | sucrose fatty acid (hydrogenated beef tallow) ester | 0.0017 | 0.51 | 0.51 | 1/300 | 1/300 | 1:1 | 92 |
| Sodium L-lauroyl-sarcosine | decaglycerine penta-stearate | 0.0017 | 0.51 | 0.51 | 1/300 | 1/300 | 1:1 | 51 |
| Sodium L-lauroyl-sarcosine | POE(30) phytosterol | 0.0017 | 0.51 | 0.51 | 1/300 | 1/300 | 1:1 | 47 |
| Sodium L-lauroyl-sarcosine | POE(30) POP(6) decyl tetradecyl ether | 0.0017 | 0.51 | 0.51 | 1/300 | 1/300 | 1:1 | 80 |
| Sodium L-lauroyl-sarcosine | POE(30) octyl phenyl ether | 0.0017 | 0.51 | 0.51 | 1/300 | 1/300 | 1:1 | 79 |
| Sodium L-lauroyl-sarcosine | POE(20) sorbitol beeswax | 0.0017 | 0.51 | 0.51 | 1/300 | 1/300 | 1:1 | 75 |
| Sodium L-lauroyl-sarcosine | sorbitan sesqui-oleate | 0.0017 | 0.51 | 0.51 | 1/300 | 1/300 | 1:1 | 41 |

As shown in Table 1, when the ratio of mutanase to the N-acyl sarcosinate was 1:300 and the ratio of mutanase to various nonionic surfactants was 1:300, namely, when the N-acyl sarcosinate and the nonionic surfactant were mixed in the ratio of 1:1 and the mixture was allowed to stand with mutanase, among the nonionic surfactants, by using polyoxyethylene sorbitol fatty acid ester, polyoxyethylene glycerin fatty acid ester, polyoxyethylene lanolin derivative, polyoxyethylene nonyl phenyl formaldehyde condensate, polyoxyethylene-polyoxypropylene block copolymer, polyoxyethylene sorbitan fatty acid ester, polyoxyethylene hydrogenated castor oil, polyoxyethylene castor oil, polyethylene glycol fatty acid ester or polyoxyethylene alkyl ether, mutanase was stabilized in the same degree as or more improved degree than that obtained by using the N-acyl sarcosinate together with sucrose fatty acid ester.

EXPERIMENT 2

Next, by using the N-acyl sarcosinate having different alkyl chain lengths and polyoxyethylene alkyl ether which showed particularly excellent stabilization effect among various nonionic surfactants, the same test as described in Table 1 was carried out by varying the ratio of the anionic surfactant to the nonionic surfactant as well as the ratio of enzyme to the anionic and nonionic surfactants. The results are shown in Table 2.

TABLE 2

| Surfactant Anion | Surfactant Nonion | Amount of enzyme (wt %) | Surfactant Amount of anion (wt %) | Surfactant Amount of nonion (wt %) | Ratio of enzyme/surfactant Anion | Ratio of enzyme/surfactant Nonion | Ratio of anion/nonion | Ratio of activity (%) |
|---|---|---|---|---|---|---|---|---|
| Sodium | POE(9) lauryl | 0.0017 | 0.51 | 0.51 | 1/300 | 1/300 | 1:1 | 95 |

TABLE 2-continued

| Surfactant | | Amount of enzyme (wt %) | Surfactant | | Ratio of enzyme/surfactant | | Ratio of anion/nonion | Ratio of activity (%) |
|---|---|---|---|---|---|---|---|---|
| Anion | Nonion | | Amount of anion (wt %) | Amount of nonion (wt %) | Anion | Nonion | | |
| Sodium N-myristoyl-sarcosinate | POE(9) lauryl ether | 0.0017 | 0.51 | 0.51 | 1/300 | 1/300 | 1:1 | 96 |
| Sodium N-palmitoyl-sarcosinate | POE(9) lauryl ether | 0.0017 | 0.51 | 0.51 | 1/300 | 1/300 | 1:1 | 96 |
| Sodium N-stearoyl-sarcosinate | POE(9) lauryl ether | 0.0017 | 0.51 | 0.51 | 1/300 | 1/300 | 1:1 | 96 |
| Potassium L-lauroyl-sarcosinate | POE(9) lauryl ether | 0.0017 | 0.51 | 0.51 | 1/300 | 1/300 | 1:1 | 95 |
| Sodium L-lauroyl-sarcosinate | POE(9) lauryl ether | 0.0017 | 0.204 | 0.816 | 1/120 | 1/480 | 1:4 | 94 |
| Sodium L-lauroyl-sarcosinate | POE(9) lauryl ether | 0.0017 | 0.340 | 0.680 | 1/200 | 1/400 | 1:2 | 94 |
| Sodium L-lauroyl-sarcosinate | POE(9) lauryl ether | 0.0017 | 0.510 | 0.510 | 1/300 | 1/300 | 1:1 | 95 |
| Sodium L-lauroyl-sarcosinate | POE(9) lauryl ether | 0.0017 | 0.638 | 0.382 | 1/375 | 1/225 | 5:3 | 95 |
| Sodium L-lauroyl-sarcosinate | POE(9) lauryl ether | 0.0017 | 0.850 | 0.170 | 1/500 | 1/100 | 5:1 | 95 |
| Sodium L-lauroyl-sarcosinate | POE(9) lauryl ether | 0.0017 | 0.918 | 0.102 | 1/540 | 1/60 | 9:1 | 79 |

As shown in Table 2, the effect for stabilization of mutanase was not changed by varying the alkyl chain length of the N-acyl sarcosinate or by converting the salt portion thereof.

As the result of the same test carried out by varying the ratio of the N-acyl sarcosinate to the nonionic surfactant, stabilization of mutanase is observed when the ratio of the N-acyl sarcosinate to the nonionic surfactant is not more than 5:1 (in the direction of decrease in the amount of the N-acyl sarcosinate and mutanase activity is inhibited when the amount of the N-acyl sarcosinate is further increased.

EXPERIMENT 3

Next, the same test was carried out by using the ratio which showed high stabilization in the combination system of the N-acyl sarcosinate and polyoxyethylene lauryl ether, namely, the ratio of the anionic surfactant to the nonionic surfactant of 5:1 with varying the ratio to the enzyme.

As a result, as shown in Table 3, it was recognized that mutanase was stabilized when the ratio of the anionic surfactant to the nonionic surfactant was 5:1 and the ratio of enzyme to the anionic surfactant was 1:3000 and the amount of the anionic surfactant was not more than 3% by weight based on the total weight of the composition.

TABLE 3

| Surfactant | | Amount of enzyme (wt %) | Surfactant | | Ratio of enzyme/surfactant | | Ratio of anion/nonion | Ratio of activity (%) |
|---|---|---|---|---|---|---|---|---|
| Anion | Nonion | | Amount of anion (wt %) | Amount of nonion (wt %) | Anion | Nonion | | |
| Sodium L-lauroyl sarcosinate | POE(9) lauryl ether | 0.001 | 0.5 | 0.1 | 1/500 | 1/100 | 5:1 | 95 |
| Sodium L-lauroyl sarcosinate | POE(9) lauryl ether | 0.001 | 1.0 | 0.2 | 1/1000 | 1/200 | 5:1 | 95 |
| Sodium L-lauroyl sarcosinate | POE(9) lauryl ether | 0.001 | 2.0 | 0.4 | 1/2000 | 1/400 | 5:1 | 92 |
| Sodium L-lauroyl sarcosinate | POE(9) lauryl ether | 0.001 | 3.0 | 0.6 | 1/3000 | 1/600 | 5:1 | 91 |
| Sodium L-lauroyl sarcosinate | POE(9) lauryl ether | 0.001 | 4.0 | 0.8 | 1/4000 | 1/800 | 5:1 | 75 |
| Sodium L-lauroyl sarcosinate | POE(9) lauryl ether | 0.1 | 0.5 | 0.1 | 1/5 | 1/1 | 5:1 | 97 |
| Sodium | POE(9) lauryl | 0.1 | 1.0 | 0.2 | 1/10 | 1/2 | 5:1 | 97 |

TABLE 3-continued

| Surfactant | | Amount of enzyme | Surfactant | | Ratio of enzyme/surfactant | | Ratio of | Ratio of |
|---|---|---|---|---|---|---|---|---|
| Anion | Nonion | (wt %) | Amount of anion (wt %) | Amount of nonion (wt %) | Anion | Nonion | anion/nonion | activity (%) |
| L-lauroyl sarcosinate | ether | | | | | | | |
| Sodium L-lauroyl sarcosinate | POE(9) lauryl ether | 0.1 | 2.0 | 0.4 | 1/20 | 1/4 | 5:1 | 95 |
| Sodium L-lauroyl sarcosinate | POE(9) lauryl ether | 0.1 | 3.0 | 0.6 | 1/30 | 1/6 | 5:1 | 90 |
| Sodium L-lauroyl sarcosinate | POE(9) lauryl ether | 0.1 | 4.0 | 0.8 | 1/40 | 1/8 | 5:1 | 72 |

Next, the results of tests for stabilization of mutanase by using the N-acyl-L-glutamate in combination with the nonionic surfactant are illustrated.

EXPERIMENT 4

According to the same manner as described in Experiment 1, mutanase (17 mg, 6,500 units/g) derived from Pseudomonas sp. strain (FERM P-4273) was dissolved in 0.1 M acetate buffer solution (500 ml, pH 5.7) to obtain an enzyme solution. The enzyme solution (10 ml) was admixed with each solution (10 ml) of various surfactants as shown in Table 4. The mixture was allowed to stand at 25° C. in a water bath for 3 hours and then enzyme activity in the mixture was determined. By taking the initial mutanase activity in a reaction system containing no surfactant as 100%, relative ratio of mutanase activity in a reaction system containing the surfactant was determined. The results are shown in Table 4.

TABLE 4

| Surfactant | | Amount of enzyme | Surfactant | | Ratio of enzyme/surfactant | | Ratio of | Ratio of |
|---|---|---|---|---|---|---|---|---|
| Anion | Nonion | (wt %) | Amount of anion (wt %) | Amount of nonion (wt %) | Anion | Nonion | anion/nonion | activity (%) |
| no surfactant is added | | 0.0017 | — | — | — | — | — | 100 |
| Monosodium-N-lauroyl-L-glutamate | POE(60) sorbitol tetraoleate | 0.0017 | 0.51 | 0.51 | 1/300 | 1/300 | 1:1 | 94 |
| Monosodium-N-lauroyl-L-glutamate | POE(15) glycerin monostearate | 0.0017 | 0.51 | 0.51 | 1/300 | 1/300 | 1:1 | 99 |
| Monosodium-N-lauroyl-L-glutamate | POE lanolin | 0.0017 | 0.51 | 0.51 | 1/300 | 1/300 | 1:1 | 90 |
| Monosodium-N-lauroyl-L-glutamate | POE nonyl phenyl formaldehyde condensate | 0.0017 | 0.51 | 0.51 | 1/300 | 1/300 | 1:1 | 99 |
| Monosodium-N-lauroyl-L-glutamate | POE(196) POP(67) block copolymer | 0.0017 | 0.51 | 0.51 | 1/300 | 1/300 | 1:1 | 90 |
| Monosodium-N-lauroyl-L-glutamate | POE(20) sorbitan monooleate | 0.0017 | 0.51 | 0.51 | 1/300 | 1/300 | 1:1 | 98 |
| Monosodium-N-lauroyl-L-glutamate | POE(20) hydrogenated castor oil | 0.0017 | 0.51 | 0.51 | 1/300 | 1/300 | 1:1 | 89 |
| Monosodium N-lauroyl-L-glutamate | POE(60) castor oil | 0.0017 | 0.51 | 0.51 | 1/300 | 1/300 | 1:1 | 91 |
| Monosodium N-lauroyl-L-glutamate | POE(40) monostearate | 0.0017 | 0.51 | 0.51 | 1/300 | 1/300 | 1:1 | 89 |
| Monosodium N-lauroyl-L-glutamate | POE(9) lauryl ether | 0.0017 | 0.51 | 0.51 | 1/300 | 1/300 | 1:1 | 95 |
| Monosodium N-lauroyl-L-glutamate | decaglycerine pentastearate | 0.0017 | 0.51 | 0.51 | 1/300 | 1/300 | 1:1 | 32 |
| Monosodium N-lauroyl-L-glutamate | POE(30) phytosterol | 0.0017 | 0.51 | 0.51 | 1/300 | 1/300 | 1:1 | 33 |
| Monosodium N-lauroyl-L-glutamate | POE(30) POP(6) decyl tetradecyl ether | 0.0017 | 0.51 | 0.51 | 1/300 | 1/300 | 1:1 | 40 |

TABLE 4-continued

| Anion | Nonion | Amount of enzyme (wt %) | Surfactant Amount of anion (wt %) | Surfactant Amount of nonion (wt %) | Ratio of enzyme/surfactant Anion | Ratio of enzyme/surfactant Nonion | Ratio of anion/nonion | Ratio of activity (%) |
|---|---|---|---|---|---|---|---|---|
| Monosodium N-lauroyl-L-glutamate | POE(30) octyl phenyl ether | 0.0017 | 0.51 | 0.51 | 1/300 | 1/300 | 1:1 | 49 |
| Monosodium N-lauroyl-L-glutamate | POE(20) sorbitol beeswax | 0.0017 | 0.51 | 0.51 | 1/300 | 1/300 | 1:1 | 47 |
| Monosodium N-lauroyl-L-glutamate | sucrose fatty acid (hydrogenated beef tallow) ester | 0.0017 | 0.51 | 0.51 | 1/300 | 1/300 | 1:1 | 52 |
| Monosodium N-lauroyl-L-glutamate | sorbitan sesqui-oleate | 0.0017 | 0.51 | 0.51 | 1/300 | 1/300 | 1:1 | 25 |
| Monosodium N-lauroyl-L-glutamate | — | 0.0017 | 0.51 | — | 1/300 | — | — | 5 |

As shown in Table 4, when the ratio of mutanase to monosodium N-lauroyl-L-glutamate was 1:300 and the ratio of mutanase to various nonionic surfactants was 1:300, namely, when monosodium N-lauroyl-L-glutamate and the nonionic surfactant were mixed together in the ratio of 1:1 and allowed to be stand with mutanase, the stability of mutanase was specifically improved by using, among the nonionic surfactants, polyoxyethylene sorbitol fatty acid ester, polyoxyethylene glycerin fatty acid ester, polyoxyethylene lanolin derivative, polyoxyethylene nonyl phenyl formaldehyde condensate, polyoxyethylene-polyoxypropylene block copolymer, polyoxyethylene sorbitan fatty acid ester, polyoxyethylene hydrogenated castor oil, polyoxyethylene castor oil, polyethylene glycol fatty acid ester or polyoxyethylene alkyl ether.

EXPERIMENT 5

Next, according to the same manner as described in Table 4, the test was carried out by using N-acyl-L-glutamate having different fatty acids and salts and polyoxyethylene alkyl ether and polyoxyethylene sorbitan fatty acid ester which showed particularly excellent stabilization among the nonionic surfactant and by varying the ratio of the anionic surfactant to the nonionic surfactant as well as the ratio of the enzyme to the anionic and nonionic surfactant. The results are shown in Table 5.

TABLE 5

| Surfactant Anion | Surfactant Nonion | Amount of enzyme (wt %) | Surfactant Amount of anion (wt %) | Surfactant Amount of nonion (wt %) | Ratio of enzyme/surfactant Anion | Ratio of enzyme/surfactant Nonion | Ratio of anion/nonion | Ratio of activity (%) |
|---|---|---|---|---|---|---|---|---|
| Monosodium N-lauroyl-L-glutamate | POE(20) sorbitan monooleate | 0.0017 | 0.51 | 0.51 | 1/300 | 1/300 | 1:1 | 98 |
| Monosodium N-coconut oil fatty acid acyl-L-glutamate | POE(20) sorbitan monooleate | 0.0017 | 0.51 | 0.51 | 1/300 | 1/300 | 1:1 | 97 |
| Monotriethanolamine N-coconut oil fatty acid acyl-L-glutamate | POE(20) sorbitan monooleate | 0.0017 | 0.51 | 0.51 | 1/300 | 1/300 | 1:1 | 96 |
| Monosodium N-stearoyl-L-glutamate | POE(20) sorbitan monooleate | 0.0017 | 0.51 | 0.51 | 1/300 | 1/300 | 1:1 | 97 |
| Monosodium N-lauroyl-L-glutamate | POE(20) sorbitan monooleate | 0.0017 | 0.204 | 0.816 | 1/120 | 1/480 | 1:4 | 97 |
| Monosodium N-lauroyl-L-glutamate | POE(20) sorbitan monooleate | 0.0017 | 0.340 | 0.680 | 1/200 | 1/400 | 1:2 | 97 |
| Monosodium N-lauroyl-L-glutamate | POE(20) sorbitan monooleate | 0.0017 | 0.510 | 0.510 | 1/300 | 1/300 | 1:1 | 98 |
| Monosodium N-lauroyl-L-glutamate | POE(20) sorbitan monooleate | 0.0017 | 0.638 | 0.382 | 1/375 | 1/225 | 5:3 | 99 |
| Monosodium N-lauroyl-L-glutamate | POE(20) sorbitan monooleate | 0.0017 | 0.850 | 0.170 | 1/500 | 1/100 | 5:1 | 99 |
| Monosodium N-lauroyl-L-glutamate | POE(20) sorbitan monooleate | 0.0017 | 0.918 | 0.102 | 1/540 | 1/60 | 9:1 | 90 |
| Monosodium N-lauroyl-L-glutamate | POE(20) sorbitan monooleate | 0.0017 | 0.969 | 0.051 | 1/570 | 1/30 | 20:1 | 76 |
| Monosodium N-lauroyl-L-glutamate | POE(9) lauryl ether | 0.0017 | 0.204 | 0.816 | 1/120 | 1/480 | 1:4 | 94 |
| Monosodium N-lauroyl-L-glutamate | POE(9) lauryl ether | 0.0017 | 0.340 | 0.680 | 1/200 | 1/400 | 1:2 | 95 |

TABLE 5-continued

| Surfactant | | Amount of enzyme (wt %) | Surfactant | | Ratio of enzyme/surfactant | | Ratio of anion/nonion | Ratio of activity (%) |
|---|---|---|---|---|---|---|---|---|
| Anion | Nonion | | Amount of anion (wt %) | Amount of nonion (wt %) | Anion | Nonion | | |
| Monosodium N-lauroyl-L-glutamate | POE(9) lauryl ether | 0.0017 | 0.510 | 0.510 | 1/300 | 1/300 | 1:1 | 95 |
| Monosodium N-lauroyl-L-glutamate | POE(9) lauryl ether | 0.0017 | 0.638 | 0.382 | 1/375 | 1/225 | 5:3 | 97 |
| Monosodium N-lauroyl-L-glutamate | POE(9) lauryl ether | 0.0017 | 0.850 | 0.170 | 1/500 | 1/100 | 5:1 | 97 |
| Monosodium N-lauroyl-L-glutamate | POE(9) lauryl ether | 0.0017 | 0.918 | 0.102 | 1/540 | 1/60 | 9:1 | 89 |
| Monosodium N-lauroyl-L-glutamate | POE(9) lauryl ether | 0.0017 | 0.969 | 0.051 | 1/570 | 1/30 | 20:1 | 73 |

As shown in Table 5, the effect for stabilization of mutanase was not changed by varying the fatty acid of N-acyl-L-glutamate and by converting the salt portion thereof.

As the results of the test carried out by converting the ratio of the N-acyl-L-glutamate to the nonionic surfactant, stabilization of mutanase is observed when the ratio of the N-acyl-L-glutamate to the nonionic surfactant is not more than 9:1 (in the direction of decrease in the amount of the N-acyl-L-glutamate), and mutanase activity is inhibited when the amount of N-acyl-L-glutamate is further increased.

EXPERIMENT 6

Next, a test was carried out by using the ratio which showed high stabilization in a combination system of the N-acyl-L-glutamate and polyoxyethylene sorbitan fatty acid ester, namely, the ratio of the anionic surfactant to the nonionic surfactant of 5:1 and varying the ratio to enzyme.

As a result, as shown in Table 6, it was recognized that mutanase was stabilized when the ratio of the anionic surfactant to the nonionic surfactant was 5:1 and the ratio of enzyme to the anionic surfactant was 1:3000 as well as the amount of the anionic surfactant was not more than 3% by weight based on the total weight of the composition.

TABLE 6

| Surfactant | | Amount of enzyme (wt %) | Surfactant | | Ratio of enzyme/surfactant | | Ratio of anion/nonion | Ratio of activity (%) |
|---|---|---|---|---|---|---|---|---|
| Anion | Nonion | | Amount of anion (wt %) | Amount of nonion (wt %) | Anion | Nonion | | |
| Monosodium N-lauroyl-L-glutamate | POE(20) sorbitan monooleate | 0.001 | 0.5 | 0.1 | 1/500 | 1/100 | 5:1 | 98 |
| Monosodium N-lauroyl-L-glutamate | POE(20) sorbitan monooleate | 0.001 | 1.0 | 0.2 | 1/1000 | 1/200 | 5:1 | 99 |
| Monosodium N-lauroyl-L-glutamate | POE(20) sorbitan monooleate | 0.001 | 2.0 | 0.4 | 1/2000 | 1/400 | 5:1 | 97 |
| Monosodium N-lauroyl-L-glutamate | POE(20) sorbitan monooleate | 0.001 | 3.0 | 0.6 | 1/3000 | 1/600 | 5:1 | 90 |
| Monosodium N-lauroyl-L-glutamate | POE(20) sorbitan monooleate | 0.001 | 4.0 | 0.8 | 1/4000 | 1/800 | 5:1 | 76 |
| Monosodium N-lauroyl-L-glutamate | POE(20) sorbitan monooleate | 0.1 | 0.5 | 0.1 | 1/5 | 1/1 | 5:1 | 98 |
| Monosodium N-lauroyl-L-glutamate | POE(20) sorbitan monooleate | 0.1 | 1.0 | 0.2 | 1/10 | 1/2 | 5:1 | 98 |
| Monosodium N-lauroyl-L-glutamate | POE(20) sorbitan monooleate | 0.1 | 2.0 | 0.4 | 1/20 | 1/4 | 5:1 | 95 |
| Monosodium N-lauroyl-L-glutamate | POE(20) sorbitan monooleate | 0.1 | 3.0 | 0.6 | 1/30 | 1/6 | 5:1 | 89 |
| Monosodium N-lauroyl-L-glutamate | POE(20) sorbitan monooleate | 0.1 | 4.0 | 0.8 | 1/40 | 1/8 | 5:1 | 72 |

The following Examples further illustrate the present invention in detail.

EXAMPLE 1

According to the following formulation, a toothpaste was prepared by a conventional method.

| Ingredients | % by weight |
| --- | --- |
| Dibasic calcium phosphate | 45.0 |
| Sorbitol | 25.0 |
| Sodium carboxymethyl cellulose | 1.0 |
| Sodium N-lauroylsarcosinate | 1.0 |
| Polyoxyethylene (60 mol) hydrogenated castor oil | 1.0 |
| Saccharin sodium | 0.2 |
| Flavor | 1.0 |
| Casein | 0.5 |
| Mutanase (10,000 units/g) | 0.1 |
| Distilled water | up to 100% |

EXAMPLE 2

According to the following formulation, a toothpaste was prepared by a conventional method.

| Ingredients | % by weight |
| --- | --- |
| Dibasic calcium phosphate | 40.0 |
| Glycerin | 20.0 |
| Carrageenan | 1.0 |
| Sodium N-lauroylsarcosinate | 1.5 |
| Polyoxyethylene (9 mol) lauryl ether | 0.9 |
| Saccharin sodium | 0.2 |
| Mutanase (1,000,000 units/g) | 0.001 |
| Distilled water | up to 100% |

EXAMPLE 3

According to the following formulation, a toothpaste was prepared by a conventional method.

| Ingredients | % by weight |
| --- | --- |
| Glycerin | 15.0 |
| Saccharin sodium | 0.03 |
| Ethanol | 3.0 |
| Flavor | 0.3 |
| Casein hydrolysate | 0.5 |
| Sodium N-myristoylsarcosinate | 0.2 |
| Polyoxyethylene (196 mol) polyoxypropylene (67 mol) block copolymer | 0.8 |
| Mutanase (1,000 units/g) | 1.0 |
| Distilled water | up to 100% |

EXAMPLE 4

According to the following formulation, a toothpaste was prepared by a conventional method.

| Ingredients | % by weight |
| --- | --- |
| Sodium percarbonate | 30.0 |
| Tartaric acid | 30.0 |
| Sodium tripolyphophate | 4.0 |
| Lactose | 34.78 |
| Sodium N-palmitoylsarcosinate | 0.5 |
| Polyoxyethylene (9 mol) lauryl ether | 0.5 |
| Magnesium stearate | 0.2 |
| Mutanase (100,000 units/g) | 0.02 |

EXAMPLE 5

According to the following formulation, a toothpaste was prepared by a conventional method.

| Ingredients | % by weight |
| --- | --- |
| Dibasic calcium phosphate | 45.0 |
| Sorbitol | 25.0 |
| Sodium carboxymethyl cellulose | 1.0 |
| Monosodium N-lauroyl-L-glutamate | 1.0 |
| Polyoxyethylene (20 mol) sorbitan monooleate | 1.0 |
| Saccharin sodium | 0.2 |
| Flavor | 1.0 |
| Casein | 0.5 |
| Mutanase (10,000 units/g) | 0.1 |
| Distilled water | up to 100% |

EXAMPLE 6

According to the following formulation, a toothpaste was prepared by a conventional method.

| Ingredients | % by weight |
| --- | --- |
| Dibasic calcium phosphate | 40.0 |
| Glycerin | 20.0 |
| Carageenan | 1.0 |
| Monosodium N-lauroyl-L-glutamate | 1.5 |
| Polyoxyethylene (9 mol) lauryl ether | 0.9 |
| Saccharin sodium | 0.2 |
| Mutanase (1,000,000 units/g) | 0.001 |
| Distilled water | up to 100% |

EXAMPLE 7

According to the following formulation, a toothpaste was prepared by a conventional method.

| Ingredients | % by weight |
| --- | --- |
| Glycerin | 15.0 |
| Saccharin sodium | 0.03 |
| Ethanol | 3.0 |
| Flavor | 0.3 |
| Casein hydrolysate | 0.5 |
| Monosodium N-coconut oil fatty acid acyl-L-glutamate | 0.2 |
| Polyoxyethylene (60 mol) hydrogenated castor oil | 0.8 |
| Mutanase (1,000 units/g) | 1.0 |
| Distilled water | up to 100% |

EXAMPLE 8

According to the following formulation, a toothpaste was prepared by a conventional method.

| Ingredients | % by weight |
| --- | --- |
| Sodium percarbonate | 30.0 |
| Tartaric acid | 30.0 |
| Sodium tripolyphophate | 4.0 |
| Lactose | 34.78 |
| Monosodium N-stearoyl-L-glutamate | 0.5 |
| Polyoxyethylene (196 mol) polyoxypropylene (67 mol) block copolymer | 0.5 |
| Magnesium stearate | 0.2 |
| Mutanase (100,000 units/g) | 0.02 |

What is claimed is:

1. An oral composition comprising mutanase and, as surfactants, a N-acyl sarcosinate or a N-acyl-L-glutamate together with one or more of nonionic surfactants selected from the group consisting of polyoxyethylene sorbitol fatty acid ester, polyoxyethylene glycerin fatty acid ester, polyoxyethylene alkyl ether, polyoxyethylene lanolin derivative, polyoxyethylene nonyl phenyl formaldehyde condensate, polyoxyethylene-polyoxypropylene block copolymer, polyoxyethylene sorbitan fatty acid ester, polyoxyethylene hydrogenated castor oil, polyoxyethylene castor oil and polyethylene glycol fatty acid ester, said mutanase being formulated in an amount of 0.001 to 10% by weight based on the total weight of the composition as that having an activity of 1,000 to 1,000,000 units/g, said N-acyl sarcosinate or N-acyl-L-glutamate being formulated in an amount of not more than 3000-fold based on the amount of mutanase to be formulated, and in an amount of 0.01 to 3% by weight based on the total amount of the composition, said nonionic surfactant being formulated in an amount that the weight ratio of said N-acyl sarcosinate to said nonionic surfactant is not more than 5:1 in the direction of decrease in the amount of said N-acyl sarcosinate, or that the weight ratio of said N-acyl-L-glutamate to said nonionic surfactant is not more than 9:1 in the direction of decrease in the amount of said N-acyl-L-glutamate, and the total amount of said N-acyl sarcosinate and said nonionic surfactant being not more than 4% by weight, or that of said N-acyl-L-glutamate and said nonionic surfactant being not more than 5% by weight.

2. An oral composition according to claim 1, wherein a N-acyl sarcosinate is formulated.

3. An oral composition according to claim 1, wherein a N-acyl-L-glutamate is formulated.

* * * * *